United States Patent
Tao et al.

[11] Patent Number: 5,096,894
[45] Date of Patent: Mar. 17, 1992

[54] RICE DEXTRIN ORAL REHYDRATION SOLUTION

[75] Inventors: Michael C. Tao; Richard E. Litov; John R. Euber; Salim S. Akrabawi; J. Roberto Moran, all of Evansville, Ind.

[73] Assignee: Bristol-Myers Squibb Co., New York, N.Y.

[21] Appl. No.: 504,142

[22] Filed: Apr. 3, 1990

[51] Int. Cl.$^5$ .................. A61K 31/715; A61K 47/40
[52] U.S. Cl. ................................. 514/58; 514/867; 536/103
[58] Field of Search ................ 514/58, 867; 536/103

[56] References Cited

U.S. PATENT DOCUMENTS 4,830,861  5/1989  Puski et al. ................. 426/629
4,942,042  7/1990  Bhargava et al. ............ 424/680

OTHER PUBLICATIONS

Lebenthal et al., J. Pediatrics, 103:29–34 (1983).
Carpenter et al., New England Journal of Medicine, 319:1346–1348 (1988).
Patra et al., Archives of Disease in Childhood, 57:910–912 (1982).
Molla, et al., The Lancet, 1317–1319 (1982).
El Mougi et al., Journal of Pediatric Gastroenterology and Nutrition, 7:572–576 (1988).
Molla et al., Journal of Pediatric Gastroenterology and Nutrition, 8:81–84 (1989).

*Primary Examiner*—Ronald W. Griffin
*Attorney, Agent, or Firm*—Robert H. Uloth

[57] ABSTRACT

An improved oral rehydration solution comprising a mixture of rice dextrin and required electrolytes is provided. The functionality of the rice dextrin in oral rehydration solutions is superior to glucose in infants with chronic diarrhea resulting in lower stool output and enhanced water retention. Rice dextrin also has a polymer profile which provides more readily available glucose than corn dextrin or rice flour. There is also provided a process for clarifying solutions of rice dextrin which involves a first filtration at 35° C. and 50° C. and a second filtration at temperatures above 80° C. using filter aid and activated carbon.

8 Claims, 1 Drawing Sheet

A Process for Preparation of Clarified Rice Syrup Solids (Rice Dextrin) for Use in Oral Rehydration Solution

RICE DEXTRIN ORAL REHYDRATION SOLUTION

BACKGROUND OF THE INVENTION

The development of oral rehydration therapy (ORT) for acute diarrheal diseases of infancy and childhood has significantly reduced related morbidity and mortality, particularly in less developed countries where it constitutes the primary mode of therapy.

Oral rehydration solutions (ORS) used in ORT generally consist of a mixture of electrolytes and a carbohydrate component such as glucose or sucrose. The American Academy of Pediatrics recommends glucose at 2.0 to 2.5% by weight, potassium at 20 mEq/L, anions as chloride and as base (acetate, lactate, citrate, or bicarbonate), sodium at 75 to 90 mEq/L for acute dehydration and sodium at 40 to 60 mEq/L for the prevention of dehydration or maintenance of hydration (1985, Pediatrics, 75:358). The World Health Organization (WHO)/UNICEF currently recommends that oral rehydration solution contains 90 mEq sodium/liter, 20 mEq potassium/liter, 80 mEq Cl/liter, 30 mEq citrate/liter or 30 mEq bicarbonate/liter and glucose 110 mmol/liter. The WHO formulation has been shown to decrease morbidity and mortality in acute diarrheal disease but the magnitude of diarrhea in terms of volume and frequency of stools and the duration of the illness is not reduced.

Substitution of other carbohydrates for glucose in WHO-type formulations has been investigated. Lebenthal, et al., J. Pediatrics., 103:29-34 (1983) studied the effect of three corn syrup sugars (dextrins) containing glucose polymers of varying lengths having dextrose equivalents of 10, 15 and 24 and determined they were suitable as the sole carbohydrate source in ORT. It has also been established that ORS in which rice and other food sources of starch are substituted for glucose are effective as reported by Carpenter, et al., New England Journal of Medicine, 319:1346-1348 (1988). In particular, rice-based oral rehydration solutions have been found to be effective as reported in the following publications.

Patra, et al Archives of Disease in Childhood, 57:910-912 (1982), "Is Oral Rice Electrolyte Solution Superior to Glucose Electrolyte Solution in Infantile Diarrhoea?"

Molla, et al The Lancet, 1317-1319 (1982), "Rice-Powder Electrolyte Solution as Oral Therapy in Diarrhoea Due to *Vibrio Cholerae* and *Escherichia Coli*".

El Mougi, et al Journal of Pediatric Gastroenterology and Nutrition, 7:572-576 (1988), "Controlled Clinical Trial on the Efficacy of Rice Powder-Based Oral Rehydration Solution on the Outcome of Acute Diarrhea in Infants".

Molla, et al Journal of Gastroenterology and Nutrition, 8:81-84 (1989), "Turning Off The Diarrhea: The Role of Food and ORS".

The rice-based ORS of the foregoing references contained from 3 to 5% rice and had electrolyte levels corresponding to conventional WHO formations. They were prepared as follows.

Patra, et al supra.—Sufficient powdered rice (prepared by popping unhusked rice on heated sand) was dissolved in rehydration fluid before use to make a 5% ORS.

Molla, et al. (1982) supra.—Rice powder was first dissolved in several hundred milliliters of water and boiled for 1-2 minutes to make a uniform solution and then electrolytes added to make a 3% ORS.

El Mougi, et al supra.—Sufficient rice powder was dissolved in 200 ml of hot water and cooked for 10 minutes until a gel formed to provide a semi-liquid 5% ORS.

Molla, et al (1989) supra.—Sufficient rice flour was boiled in 1.1 liters of water for 5 to 7 minutes forming a homogeneous solution which was mixed with electrolytes to make a 4.5% ORS.

One problem associated with the use of prior art rice-based ORS is that they must be prepared shortly before use because they are not sterile. Another problem with prior art rice ORS relates to the relative insolubility of rice flour which prevents preparation of pharmaceutically elegant crystal (water) clear ORS.

A primary object of the invention is to provide a stable ready-to-use ORS wherein the carbohydrate component is rice dextrin.

Still another object of the invention is to provide an improved rice based ORS which results in lower stool output and a better water and potassium balance during the rehydration period.

SUMMARY OF THE INVENTION

The present invention concerns an improved oral rehydration solution comprising a mixture of required electrolytes combined with rice dextrin. The invention is based on the discovery that ORS rice dextrin functions better than ORS glucose in infants with chronic diarrhea resulting in lower stool output and enhanced water retention. Rice dextrin also has a glucose polymer profile which provides more readily available glucose than corn dextrin or rice flour.

DETAILED DESCRIPTION OF THE INVENTION

Figure 1:
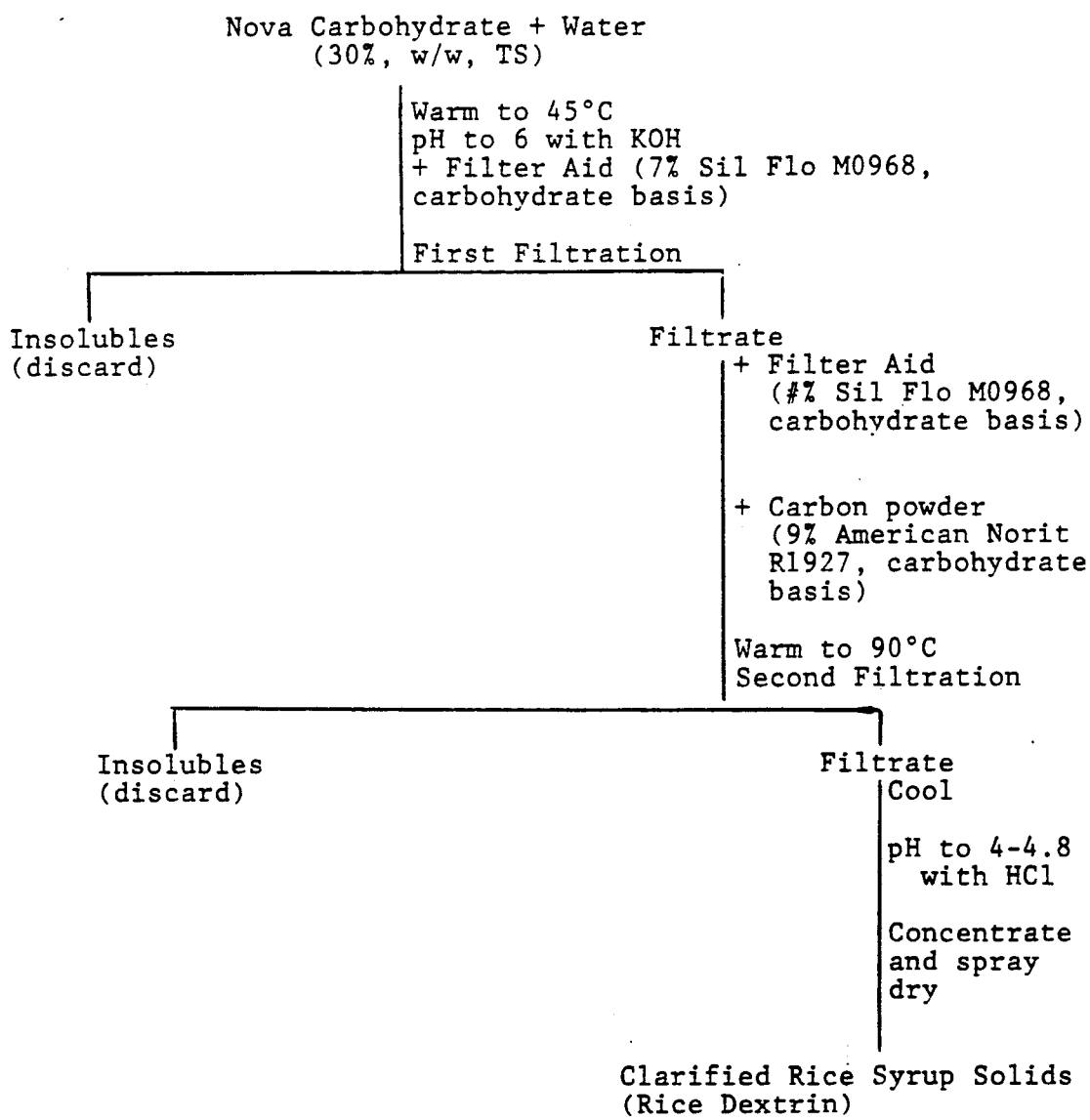
FIG. 1 is a schematic diagram of a process for clarification of rice dextrin in accordance with the invention.

The oral rehydration solution of the invention is made by preparing a solution of potassium, sodium, chloride and a base (acetate, lactate, citrate, or bicarbonate) in water. Clarified rice dextrin along with optional flavoring agents are added to the solution which is standardized with purified water to provide from 10 to 80 g/l and preferably 10-35 g/L of rice dextrin. Sodium is added at 20-100 mEq/L with a preferred level of from 40-60 mEq/L for formulations for treatment of acute dehydration and 75-90 mEq/L for formulations for prevention of dehydration or maintenance of hydration. Preferred potassium levels are from 20-30 mEq/L with a broad range of 20-100 mEq/L operable. The chloride anion is preferably added at 30-80 mEq/L with a broad range of 25-100 mEq/L operable. The base selected from the group consisting of acetate, lactate, citrate or bicarbonate is preferably added at a range of 25-40 mEq/L with a broad range of 20-50 mEq/L operable.

A most preferred rice dextrin based ORS comprises per liter: sodium—50 mEq: potassium—25 mEq: chloride—45 mEq: citrate—34 mEq; rice dextrin—30 g.

The rice dextrin glucose polymer (GP) profile of the instant ORS has a distribution of short chain glucose polymers consisting of 50 to 90% 2 to 6 glucose units and preferably 55 to 80% and most preferably 65 to 75% (Wt./Wt. basis).

Rice dextrin suitable for use in the ORS of the invention can be obtained from the solubilized rice starch of Puski et al U.S. Pat. No. 4,830,861 incorporated in entirety herein. Puski et al describe a procedure whereby the carbohydrate in rice flour is solubilized by amylase enzymes and separated from insoluble rice protein and carbohydrate by centrifugation. The resulting soluble fraction contains about 98% carbohydrate and less than 1% but more than 0.1% protein. This material is not suitable as the carbohydrate component of the instant ORS due to trace amounts of particulate matter and residual protein which contributes to foaming and browning problems during processing and sterilization and the formation of a fine precipitate during storage.

According to the instant invention, the solubilized rice carbohydrate of Puski et al was clarified by a process comprising the steps of:
(a) filtering the solubilized rice carbohydrate fraction obtained from rice flour by enzymatic hydrolysis at neutral pH using filter aid at 35° C. to 50° C.; and then
(b) subjecting the filtrate to a second filtration using filter aid and activated carbon at temperatures above 80° C.

If desired, the clarified solution can be spray dried following pH adjustment to 4.0-4.8 and preferably 4.5.

Conventional filter aids such as amorphous silica (Silflow) from Sil Flo Corporation, and activated carbon, Darco S-51, from American Norit are used. The clarified rice dextrin of the instant process may be spray dried to provide rice dextrin solids having less than 0.1% protein by weight.

The first filtration essentially reduces the protein to a level where the product can be sterilized without foaming and browning problems. However, the resulting ORS is not acceptable in that it does not have sufficient clarity to meet the requirement of a clear ORS. Subjecting the filtrate from the first filtration to a second filtration with activated carbon at high temperature, preferably at 80°-95° C. and most preferably at 90°-95° C., removes the small particulate precipitate and the haze that forms in the carbohydrate after the first filtration. The results in Table 1 show the improved clarity as a result of the second filtration above 80° C.

TABLE 1

Effect of Filtration Temperature on the Clarity of Carbohydrate Solutions at Room Temperature and 90-95° C.

| Filtration Temperature (°C.) | Visual Clarity[a] (20%, w/w, TS) | | Spectrophotometric Clarity[a] (400 nm, 20%, w/w, TS) | |
|---|---|---|---|---|
| | RT | 90-95° C. | RT | 90-95° C. |
| 40-45 | Clear | Hazy | 0.012 | 0.385 |
| 60-65 | Clear | Hazy | 0.013 | 0.271 |
| 70-75 | Clear | Hazy | 0.020 | 0.138 |
| 80-85 | Clear | Clear | 0.012 | 0.017 |
| 90-95 | Clear | Clear | 0.013 | 0.015 |

[a]Temperatures refer to the solution temperature at the time of observation or measurement.

The second filtration at a temperature below 80° C. does not remove the haze or precipitate formed in the sterilized ORS. The criticality of the second filtration temperature on the clarity of ORS is shown in Table 2 where results of a second filtration at high (90° C.) and low (45° C.) temperature are set out.

TABLE 2

The Effect of Temperature on the Clarity of Carbohydrate Solutions Prepared Using Second Filtration Temperatures of 45° C. or 90° C.

| Process Temp./ Sample Temp. | Visual Clarity (20%, w/w, TS) | Spectrophotometric Clarity (400 nm, 20%, w/w, TS |
|---|---|---|
| 45° C. Filtration | | |
| RT | Clear | 0.016 |
| 90-95° C.[a] | Hazy | 0.246 |
| Cooled to RT[b] | Slight Haze | 0.019 |
| 90° C. Filtration | | |
| RT | Clear | 0.010 |
| 90-95° C.[a] | Clear | 0.015 |
| Cooled to RT[b] | Clear | 0.014 |

[a]The solution was placed in a bath at 90-95° C. for 20 minutes and immediately examined for clarity.
[b]The solution placed in a bath at 90-95° C. was subsequently placed in a room temperature bath.

Commercially available rice syrup solids (rice dextrin) are suitable for the instant invention provided they do not contain more than 0.1% by weight protein or other particulate matter and wherein the glucose polymer (GP) profile of GP2 through GP6 is from 50 to 90%. Those that have more than 0.1% by weight protein or other particulate matter are subjected to the instant clarification process.

Table 3 sets out the distribution of glucose polymer found in samples of rice dextrin (RD) and corn dextrin (CD) with similar dextrose equivalents. Rice flour (RF) is also compared. The unclarified rice dextrin (RD-1) was opaque and had poor physical properties. Rice dextrins of the instant invention (RD-2, RD-3, RD-4) were very clear syrups. The corn dextrin syrup was also clear while the rice flour sample was insoluble and opaque.

TABLE 3

Glucose Polymer (GP) Profiles of Rice Dextrin (RD), Corn Dextrin (CD) and Rice Flour (RF) by Weight Percent

| Polymer* | Unclarified RD-1 | Production Scale | | | | |
|---|---|---|---|---|---|---|
| | | RD-2 | RD-3 | RD-4** | CD | RF |
| GP1 | 4.1 | 9.6 | 6.0 | 4.7 | 7.4 | 0.0 |
| GP2 | 11.6 | 9.8 | 14.1 | 13.5 | 7.7 | 0.0 |
| GP3 | 15.0 | 13.0 | 16.8 | 16.8 | 9.1 | 0.0 |
| GP4 | 6.5 | 7.2 | 7.1 | 8.9 | 7.5 | 0.0 |
| GP5 | 19.6 | 8.9 | 21.2 | 16.6 | 7.6 | 0.0 |
| GP6 | 10.2 | 8.0 | 6.9 | 13.6 | 7.7 | 0.0 |
| >GP7 | 32.9 | 43.4 | 27.8 | 25.9 | 53.0 | 100 |

*number designates glucose units
**clinical

Comparison of Rice Dextrin and Corn Dextrin for Use in Oral Rehydration Solutions As previously stated, the World Health Organization (WHO) recommends glucose as the carbohydrate component in oral rehydration solutions (ORS) to aid in replacement of water and electrolytes for infants with serious diarrhea. Glucose enhances the membrane transport of sodium which in turn enables rapid uptake of water.

A clinical comparison of rice dextrin ORS and glucose ORS demonstrated that rice dextrin ORS performed better in infants with diarrhea than the formulation with glucose as the carbohydrate source. Corn dextrin has also been used as the carbohydrate source in oral rehydration therapy. Lebenthal et al supra. However, as discussed below, rice dextrin provides more readily available glucose than corn dextrin in infants with chronic diarrhea.

Both rice dextrin and corn dextrin are composed of glucose polymers derived by partial hydrolysis of the parent starch. Digestion of these glucose polymers (GP) in infants involves enzymatic breakdown to glucose by amylase enzymes such as intestinal glucoamylase. This enzyme is distributed throughout the small intestinal mucosa and tends to be more resistant to intestinal injury brought about by diarrhea. Disaccharides and other low molecular weight glucose polymers found in dextrins are the preferred substrate for glucoamylase.

Table 4 shows a glucose polymer (GP) distribution for rice dextrin of the instant ORS and a commercially available corn dextrin with a similar dextrose equivalent.

TABLE 4

| Comparison of Rice GP to Corn GP Distribution by Weight Percent | | |
|---|---|---|
| | Rice GP | Corn GP |
| glucose (GP1) | 3.8 | 6.2 |
| GP2–GP6 | 65.7 | 33.6 |
| >GP6 | 30.5 | 60.1 |

It is evident from the rice dextrin GP distribution that a greater percentage (65.7%) of the total polymers are short chain polymers consisting of 2–6 glucose units (GP2–GP6) compared to the corn GP distribution (33.6%). Therefore, rice dextrins are preferred substrates over corn dextrins for glucoamylase, the primary digestive enzyme for glucose utilization after episodes of infant diarrhea.

Table 5 sets out the results of enzymatic hydrolysis of rice and corn dextrin by mucosal homogenates. In this comparison, enzymes obtained from saliva, duodenal aspirates and duodenal mucosal homogenates were obtained from several infants and pooled. Five hundred mL of carbohydrate solution were incubated with 100 mL of duodenal homogenate and incubated for 3 hours with mechanical shaking at 37° C. Following incubation, the mixtures were heated at 100° C. for 5 minutes, passed through 4 layers of millipore filters and analyzed on HPLC. The results were combined into two categories GP (2–4) and GP≧5. The results are shown in Table 5.

TABLE 5

| In Vitro Hydrolysis of Rice and Corn Dextrins By Pooled Mucosal Homogenates | | | |
|---|---|---|---|
| | Glucose | GP (2–4)* | GP >5* |
| rice | +.74 ± .19$^a$ | +1.32 ± .21$^a$ | −2.16 ± .16$^a$ |
| corn | +.22 ± .03$^b$ | +0.56 ± .19$^b$ | −0.79 ± .25$^b$ |

*glucose units
$^a$Values having different superscripts are significantly different (p <0.01)

It is evident that rice dextrin produces significantly more glucose and low molecular weight GP than corn dextrin. Correspondingly, the higher molecular weight fraction of rice dextrin (GP>5) decreased faster compared to the high molecular weight fraction of corn dextrin. These findings illustrate that with human enzyme extracts, rice GP was a better substrate for conversion to glucose and short chain GP than corn GP.

Carbohydrate Tolerance Studies

Table 6 sets out results of carbohydrate tolerance studies with sixteen infants with chronic diarrhea. The following procedure was used. The patients were fasted for eight hours and then given two grams per kg of a 10% solution of glucose, rice dextrin or corn dextrin in random order on consecutive mornings. All three of the different carbohydrates were well digested and absorbed.

TABLE 6

| Maximal Serum Glucose Response and Elapsed Time Until Peak Serum Glucose Following Oral Consumption Of Glucose, Rice Dextrin and Corn Dextrin ORS | | |
|---|---|---|
| | Maximal increase in serum glucose mg/Dl (X ± SD) | Elapsed time until peak serum glucose min (X ± SD) |
| Glucose | 41.1 ± 14.5$^a$ | 31.9 ± 7.5$^a$ |
| Rice Dextrin | 36.6 ± 7.3$^a$ | 34.0 ± 10.2$^a$ |
| Corn Dextrin | 7.6 ± 10.3$^b$ | 52.5 ± 25.7$^b$ |

$^a$Values having different superscripts are significantly different (P <0.02).

It is evident that the maximal increase in serum glucose is significantly higher with the rice dextrin solution compared to the corn dextrin solution. With respect to peak glucose serum levels, the elapsed time for rice dextrin was significantly shorter than for corn dextrin. Glucose solutions and rice dextrins have similar increase in serum glucose. However, glucose solutions have a higher osmotic load compared to dextrin solutions which may be a problem for ORS products.

Serum glucose response curves established that the mean area under the curve of the rice dextrin was significantly greater than corn dextrin during the first 30 and 60 minutes of the tolerance test (p<0.05) but not at 120 minutes.

Results of this study illustrate that rice dextrin has a greater maximal rise of serum glucose, a shorter elapsed time until the serum glucose peaked and a larger area under the serum glucose response curve during the first 30 to 60 minutes of testing than corn dextrin. These results demonstrate that rice dextrin is more rapidly hydrolyzed and absorbed than corn dextrin. Thus, rice dextrin provides more readily available glucose than corn dextrin to enable the rapid uptake of water and sodium from an oral rehydration solution.

Comparison of Clarified Rice Dextrin, Pop Rice Powder and Rice Flour

As previously mentioned, both popped rice and rice flour have been used in oral rehydration therapy. However, popped rice and rice flour are not suitable as a carbohydrate component for a clear shelf-stable ready-to-use ORS. Oral Rehydration solutions of popped rice and rice flour cannot be sterilized without foaming and browning problems associated with processing and sterilization of the products. Moreover, clear ready-to-use ORS cannot be prepared because of the relative insolubility of popped rice powder and rice flour. Finally, the organoleptic properties of popped rice or rice flour make them less desirable for ORS than rice dextrin. Comparative results of solutions of rice dextrin, pop rice powder and rice flour at 3% w/w concentration are presented in the following tables.

TABLE 7

| Soluble Solids Content of Clarified Rice Dextrin, Pop Rice Powder and Rice Flour at 25° C. Before and After an 80° C. Heat Treatment | | |
|---|---|---|
| | Soluble Solids Content (%, w/w) Temperature (°C.)$^a$ | |
| Product | 25 (1) | 25 (2) |
| Clarified Rice Dextrin | 100 | 100 |
| Pop Rice Powder | 13 | 20 |

TABLE 7-continued

Soluble Solids Content of Clarified
Rice Dextrin, Pop Rice Powder and Rice Flour
at 25° C. Before and After an 80° C. Heat Treatment

| Product | Soluble Solids Content (%, w/w) Temperature (°C.)[a] | |
|---|---|---|
| | 25 (1) | 25 (2) |
| Rice Flour | 4 | 2 |

[a]The number in parentheses refers to measurements taken before (1) and after (2) heating to 80° C.

TABLE 8

Spectrophotometric Clarity of Solutions of Rice
Dextrin, Pop Rice Powder and Rice Flour Solutions
at 25° C. Before and After an 80° C. Heat Treatment

| Product | Spectrophotometric Clarity (Absorbance, 400 nm) Temperature (°C.)[a] | |
|---|---|---|
| | 25 (1) | 25 (2) |
| Rice Dextrin | 0.002 | 0.009 |
| Pop Rice powder | 3.22 | 3.23 |
| Rice Flour | 2.54 | 2.73 |

[a]The number in parentheses refers to measurements taken before (1) and after (2) heating to 80° C.

TABLE 9

Organoleptic Evaluation of Clarified
Rice Dextrin, Pop Rice Powder and Rice Flour
Solutions at 25° C. Before and After 80° C. Heat Treatment

| Product/Attribute | Description Temperature (°C.)[c] | |
|---|---|---|
| | 25 (1) | 25 (2) |
| Clarified Rice Dextrin | | |
| Appearance | Water-like, clear solution | Same |
| Odor | Odor free | Same |
| Flavor/mouthfeel | Slight sweet, clean flavor, water-like mouthfeel | Same |
| Pop Rice Powder | | |
| Appearance | Opaque, tan colored solution. Sediment, many dark specks. Grainy appearance on glass. | Same |
| Odor | Strong wheat flour odor. Slightly unpleasant (sulfureous or wet dog). | Same |
| Flavor/mouthfeel | Strong wheat flour flavor. Gritty mouthfeel, mucilaginous, throat-clinging. | Same |
| Rice Flour | | |
| Appearance | Opaque, white colored solution. Sediment, few dark specks. Grainy appearance on glass. | Same |
| Odor | Mild wheat flour odor. | Same |
| Flavor/mouthfeel | Mild wheat flour flavor. Gritty mouthfeel | Mild wheat flour flavor. Gritty mouthfeel, mucilaginous, throat-clinging. |

[c]The number in parentheses refers to observations taken before (1) or after (2) heating to 80° C.

It is evident that rice dextrin was completely soluble while only a small fraction of the pop rice or rice flour solids was soluble. The more soluble rice dextrin relative solubility affects clarity as shown in Tables 7-8. The clarified rice dextrin solution was "water clear" while the pop rice and rice flour solutions were nearly opaque.

In the organoleptic evaluation presented in Table 9, the rice dextrin solution was significantly different from the pop rice powder and rice flour solutions with respect to all attributes examined. Heat treatment (80° C.) had little effect except for a slight influence on the mouthfeel of the rice flour solution.

Comparison of Rice Dextrin and Rice Flour Digestion by Intestinal Enzymes

Major enzymes involved in carbohydrate digestion and production of glucose from glucose polymers are intestinal maltase and pancreatic amylase. However, during the first six months of life, pancreatic amylase is absent or extremely low in concentration. Hence, carbohydrate digestion in young infants is primarily dependent on amylase in saliva along with a variety of intestinal amylases.

Gastrointestinal illness in infants affects carbohydrate digestion because of the loss of enzymes due to infectious disease. However, maltase activity remains high following infectious illness, when other disaccharidases become severely depressed. In addition, carbohydrate breakdown is affected by the low activity of pancreatic amylase in infants up to six months of age.

Table 10 sets out a comparison of maltase digestion of rice dextrin (RD) and rice flour (RF). The maltase digestions were performed by incubating (37° C.) 30 mg. of RD or RF with 20 Units of maltase in a total volume of 1.0 mL for various lengths of time. Following incubation, samples were placed in a boiling water bath for 5 minutes to inactivate the test enzyme. Digested samples were centrifuged to separate insoluble materials (e.g., RF) and the concentration of free glucose in the supernatant determined colorimetrically with a Trinder glucose oxidase reagent (Sigma Chemical Co., St. Louis, Mo.).

TABLE 10

In vitro Hydrolysis of Rice Dextrins
and Rice Flour by Maltase

| Substrate | Maltase Incubation (min) | Glucose Production (mg)[a] | |
|---|---|---|---|
| | | Total[b] | Adjusted[c] |
| Rice Flour | 0 (blank) | 0.00 | 0.00 |
| | 5 | 0.03 | 0.03 |
| | 10 | 0.00 | 0.00 |
| | 20 | 0.00 | 0.00 |
| | 40 | 0.03 | 0.03 |
| Rice Dextrin | 0 (blank) | 0.85 | 0.00 |
| | 5 | 2.97 | 2.12 |
| | 10 | 3.93 | 3.08 |
| | 20 | 4.91 | 4.06 |
| | 40 | 6.01 | 5.16 |

[a]Represents the mean of two separate assays using a total of 20 units of maltase and 30 mg of substrate.
[b]Represents total glucose detected following incubation of substrate with maltase.
[c]Represents only glucose produced directly as a result of maltase digestion (i.e., after subtracting free glucose in undigested substrate).

It is evident that no glucose was found in RF samples following digestion with maltase for up to 40 minutes. Digestion of RD with maltase, however, led to the immediate production of glucose which increased with increasing incubation times up to 40 minutes. When free glucose in undigested RD was subtracted from total glucose in digested rice dextrins, the amount of glucose liberated as a direct result of maltase digestion ranged from 2.12 to 5.16 mg or 7-17% of the total RD. These results demonstrate that glucose is produced during maltase digestion of RD but not RF.

As previously mentioned, the RD profile for the instant ORS consists of GP of 2 to 6 glucose units with from 65 to 75% preferred. RF has no GP less than 7 GP. When RF and RD are incubated with human pancreatic glucoamylase, proportional increases in GP1 through GP6 content were found for RF and RD which suggests that RF and RD are comparable in terms of pancreatic amylase digestibility. However, as pointed out above, pancreatic amylase is not important in the young infant.

Table 11 sets out a comparison of the amount of glucose in solutions of RD and RF before and after digestion with human pancreatic amylase and excess maltase further illustrating that RD provides substantially higher levels of glucose than RF in a comparative test period. Coupled enzyme digestions consisted of incubating 30 mg of RD or RF with 0.28 Units of amylase for desired times, boiling samples for 5 minutes to inactivate the amylase, and subsequent incubation of mixtures with excess maltase (50 Units) to convert available maltose (GP2) and maltotriose (GP3) to free glucose. Digested samples were centrifuged to separate insoluble materials (e.g., RF) and the concentration of free glucose colorimetrically determined.

TABLE 11

In vitro Hydrolysis of Rice Dextrins and Rice Flour with Pancreatic Amylase Followed by a Maltase Digestion Step to Generate Free Glucose

| Substrate | Amylase Incubation (min) | Glucose Production (mg)[a] Total[b] |
|---|---|---|
| Rice Flour | 0 (blank) | 0.00 |
| | 2 | 1.16 |
| | 5 | 2.01 |
| | 10 | 3.10 |
| | 20 | 5.65 |
| | 40 | 8.83 |
| Rice Dextrins | 0 (blank) | 7.00 |
| | 2 | 8.23 |
| | 5 | 9.07 |
| | 10 | 10.24 |
| | 20 | 11.80 |
| | 40 | 13.73 |

[a]Represents the mean of two separate assays using a total of 0.28 Units of human pancreatic amylase and 30 mg of substrate.
[b]Represents total glucose detected following incubation of substrate with maltase and amylase.

It is evident that incubation of RD or RF with excessive levels of maltase alone (amylase blank) resulted in production of large amounts of glucose in RD samples (7 mg/30 mg RD), 23% of total RD but no glucose in maltase digested RF. This glucose is the result of maltase digestion of GP2 (maltose) and GP3 (maltotriose) which is present in RD but not RF. Digestion of RD or RF with both pancreatic amylase and excess maltase led to higher amounts of glucose in RD samples than in RF samples. The total glucose produced in samples of RD or RF increased with increasing time of incubation with amylase.

The results from the intestinal digestion study indicate that higher levels of glucose are produced from RD than RF during digestion by both amylase and maltase. Further, the results also demonstrate that glucose is produced during maltase digestion of RD but not RF indicating that free glucose would continue to be available from RD but not RF during periods of pancreatic amylase insufficiency. Thus, "in vitro" digestion of RD but not RF appears to provide the glucose required in the management of acute diarrhoeal dehydration in infants.

The following examples illustrate the invention.

EXAMPLE 1

Clarification of Rice Dextrin—Lab Scale

In this example, 300 g of a solution containing 30% crude rice dextrin carbohydrate is warmed to 45° C. and the pH adjusted to 6.0 with KOH. A first filtration is carried out with a Buckner filtration funnel precoated with filter aid after the addition of 6.2 g filter aid, Sil Flo.

The filtrate is prepared for a second filtration by the addition of 2.75 g of filter aid and 8.1 g of carbon powder, American Norit. The mixture is heated to 90° C. before being filtered on a Buchner filtration funnel coated with filter aid.

The resulting filtrate is cooled to 30° C. and the pH is adjusted to 4.0–4.5 with 0.1N HCl. This clear filtrate is used in ORS products. The processed carbohydrate solutions are clear and colorless at 20% solids and the protein content is <0.1% on a solids basis.

EXAMPLE 2

Clarification of Rice Dextrin—Production Scale

Crude rice dextrins, a by-product of the high protein rice flour process, require clarification prior to utilization in a commercial ORS product. In this production scale clarification example, 4500 pounds of crude rice dextrins are blended into an open tank containing 1250 gallons of defluoridated tap water. The mixture is agitated and heated to 112°-122° F.

The pH is adjusted to 5.9 with a 10% solution of KOH. In this case, the initial pH was 4.5 and 6 pounds of KOH was required to bring the pH to 5.98. Approximately 300 pounds of Silflo filter aid was added to the water and rice dextrin mixture in the open tank. A plate and frame filter press is assembled with about 50 pounds of Silflo filter aid used to coat the filters. The rice dextrin solution is pumped through the filter press into a second open tank. The agitator is started in the second tank containing the first filtrate at about 25% solids and this filtrate is heated to 185° F.

After the first filtrate reaches the desired temperature, 84 pounds of Silflo filter aid and 253 pounds of activated carbon are added. This solution is pumped through a properly assembled plate and frame filter coated with filter aid to a third tank where the second filtrate is first cooled to 100° F. in the tank, then to 45° F. through a plate cooler. The cooled second filtrate at 17 91% total solids is adjusted to pH 4.5 with a 10% solution of HCl. This second filtrate is concentrated and spray dried to produce a white powder with about 2.3% moisture, less than 0.1% protein and a 24.6 dextrose equivalent (DE). When reconstituted, it is crystal (water) clear.

EXAMPLE 3

Preparation of Rice Dextrin Oral Rehydration Solution

Oral Rehydration Solution (ORS) is formulated and manufactured on a production scale using the following procedure for a 2000 gallon batch.

Initially, 1800 gallons of deionized water is heated to 130° F. and pumped into a blending tank. Then, the dry ingredients, 19.7 kg sodium chloride, 3710 g sodium citrate, 1920 g citric acid, 18.6 kg potassium citrate and 233.5 kg dry, clarified rice syrup solids are added to the water through a Tri-Blender.

After the dry ingredients are added, 21.2 kg of Natural Tropical Flavor liquid is added to the product in the blending tank. The blended product is then pumped through the cooler at 40° F. The product is standardized with purified water to an optimum total solids of 3.49%. Approximately 200 gallons of water is required to standardize the product.

The liquid product is filled into containers for sterilization. The nutrient claims per liter are listed as follows:

| Claims Per Liter | | |
|---|---|---|
| Sodium | mEq. | 50 |
| Chloride | mEq. | 45 |
| Potassium | mEq. | 25 |
| Citrate | mEq. | 34 |
| Rice dextrins | g | 30 |
| Calories | kcal | 120 |

EXAMPLE 4

Clinical Comparison of Rice Dextrin ORS and Glucose ORS

A clinical study was carried out to evaluate the efficacy of the rice dextrin ORS of the instant invention compared to the conventional glucose-based ORS as follows.

Male infants, 3-18 months of age, with mild to moderate dehydration secondary to acute diarrhea were selected as candidates for ORT and randomly divided into two groups. Initial information obtained on all patients was age, sex, weight, initial degree of dehydration, days of diarrhea prior to enrollment, and presence or absence of vomiting. Baseline blood samples were collected for determinations of serum sodium, potassium, chloride, bicarbonate, pH, $pCO_2$, glucose, urea, creatinine, and osmolality. Additional determinations were performed at 6, 12, 24, and 48 hours after admission. During the study period, stool and urine were collected separately, weighed, and stored for determination of sodium and potassium: stool for osmolality, and urine for specific gravity. Collection periods of stool and urine were from 0-6 hours, 6-12 hours, and 12-24 hours. Vomitus weights were estimated by determining the difference between the dry and wet weights of diapers utilized to collect the vomitus.

On admission to the study, the infants total fluid deficit was determined by multiplying estimated percentage of dehydration by the admission weight. During the ensuing 6-12 hours, infants received the ORS in a volume equivalent to twice the calculated fluid deficit. When clinically indicated, such as in infants reluctant to drink or who vomited frequently, the ORS was given by means of a nasogastric tube. After the administration of the calculated volume of fluid, the infants were reassessed by clinical examination. If rehydration was not achieved, a volume of rehydration solution was given again, calculated according to the more recent estimate of fluid deficit with intake recorded throughout the period of rehydration.

Upon completion of rehydration, the patients were weighed and the percentage of weight gain for each infant was calculated as follows: ((rehydration weight-admission weight)/rehydration weight) times 100.

Non-parametric data was analyzed by the chi-square test. Continuous data was analyzed by ANOVA or repeated measure analysis of varients for treatment differences over time. A level of significance was set at $p<0.05$. Results are expressed as mean ± one standard deviation (SD) unless otherwise indicated.

Table 12 below sets out the composition of the oral rehydration solution used in this study.

TABLE 12

| Composition of Oral Rehydration Solution | | |
|---|---|---|
| | Rice Dextrin | Glucose |
| Sodium (mmol/L) | 50 | 75 |
| Potassium (mmol/L) | 25 | 20 |
| Chloride (mmol/L) | 45 | 65 |
| Citrate (mmol/L) | 10 | 10 |
| Glucose (g/L) | — | 25 |
| Rice Syrup Solids (g/L) | 30 | — |
| Osmolality (mOsm/kg) | 200 | 305 |

Table 13 illustrates there were no significant differences in the clinical features and nutritional status of the study groups.

TABLE 13

| Clinical Features of patients on Entry into the Study | | |
|---|---|---|
| Variables | Rice Dextrin (n = 30) | Glucose (n = 29) |
| Age, month | 9.8 ± 4.1 | 9.8 ± 4.2 |
| Weight, kg | 7.2 ± 1.6 | 7.8 ± 1.6 |
| Duration of diarrhea, days | 2.5 ± 1.5 | 2.8 ± 1.8 |
| Number of stools/day | 12 | 15 |
| Estimated dehydration (% patients enrolled) | | |
| Mild | 19 | 19 |
| Moderate | 17 | 14 |

Table 14 sets out results of balance studies for fluid and sodium intake. Both groups of patients were comparable with respect to ORS intake over the study period. Glucose ORS patients received an ORS with higher concentration of sodium. Thus, their net sodium intake was significantly higher than the intake of patients given rice dextrin ORS.

TABLE 14

| Fluid and Sodium Intake During Study | | |
|---|---|---|
| Variables | Rice Dextrin (n = 30) | Glucose (n = 29) |
| Fluid (mL/kg) | | |
| 0-6 hours | 108 ± 9 | 104 ± 9 |
| 0-12 hours | 82 ± 6 | 80 ± 6 |
| 0-48 hours | 105 ± 7 | 107 ± 7 |
| Sodium (mmol/kg) | | |
| 0-6 hours | 5.2 ± 0.4 | 7.6 ± 0.7* |
| 0-12 hours | 3.9 ± 0.4 | 5.4 ± 0.4* |
| 0-48 hours | 4.4 ± 0.4 | 6.5 ± 0.4* |

Values represent Mean ± SEM
*Significantly different $P <0.05$

Table 15 sets out the stool output. During first six hours of treatment, the mean stool output was lower in rice dextrin ORS patients. The mean stool output over the entire study period for rice dextrin group was 49.9 g/kg compared to 65.9 g/kg for the glucose ORS group. Stool output of sodium and potassium was significantly lower in the rice dextrin ORS group when compared to the glucose group during the first six hours of treatment.

There was a trend towards lower stool weight and Na output at the later time periods of 6-12, 12-24, and 24-48 hours for the rice dextrin ORS group.

TABLE 15

| | Stool Output | |
|---|---|---|
| | Groups | |
| Variables | Rice Dextrin (n = 30) | Glucose (n = 29) |
| Weight (g/kg) | | |
| 0-6 hours | 28.7 ± 4.1 | 45.5 ± 6.7* |
| 6-12 hours | 29.1 ± 3.6 | 32.0 ± 6.2 |
| 12-24 hours | 55.0 ± 5.6 | 68.5 ± 10.1 |
| 24-48 hours | 86.7 ± 11.9 | 117.6 ± 20.5 |
| Na (mmol/kg) | | |
| 0-6 hours | 1.38 ± 0.25 | 2.88 ± 0.65* |
| 6-12 hours | 1.39 ± 0.21 | 1.90 ± 0.46 |
| 12-24 hours | 2.39 ± 0.27 | 4.15 ± 0.67 |
| 24-48 hours | 4.24 ± 0.70 | 6.81 ± 1.40 |
| K (mmol/kg) | | |
| 0-6 hours | 1.02 ± 0.14 | 1.45 ± 0.16* |
| 6-12 hours | 0.99 ± 0.13 | 0.97 ± 0.17 |
| 12-24 hours | 1.81 ± 0.17 | 1.83 ± 0.30 |
| 24-48 hours | 2.75 ± 0.32 | 3.04 ± 0.66 |

Values represent Mean ± SEM.
*Statistically different $p < 0.05$

Table 16 sets out the net gut balance calculated by subtracting stool output from net intake.

TABLE 16

| | Net Gut Balance | |
|---|---|---|
| | Groups | |
| Variables | Rice Dextrin (n = 30) | Glucose (n = 29) |
| Fluid (mL/kg) | | |
| 0-6 hours | 79.4 ± 6.5* | 58.6 ± 5.2 |
| 6-12 hours | 25.6 ± 6.0 | 24.2 ± 4.1 |
| 12-24 hours | 46.7 ± 5.6 | 21.8 ± 4.9 |
| 24-48 hours | 69.0 ± 7.1 | 61.3 ± 6.9 |
| Sodium (mmol/kg) | | |
| 0-6 hours | 3.74 ± 0.36 | 4.75 ± 0.51 |
| 6-12 hours | 0.95 ± 0.38 | 1.26 ± 0.22 |
| 12-24 hours | 1.46 ± 0.36 | 1.30 ± 0.40 |
| 24-48 hours | 2.29 ± 0.51 | 3.04 ± 0.93 |
| Potassium (mmol/kg) | | |
| 0-6 hours | 1.59 ± 0.23* | 0.63 ± 0.13 |
| 6-12 hours | 0.36 ± 0.21 | 0.22 ± 0.16 |
| 12-21 hours | 0.42 ± 0.18 | 0.16 ± 0.21 |
| 24-48 hours | 1.00 ± 0.26 | 0.75 ± 0.35 |

Values represent Mean ± SEM.
*Statistically different $p < 0.05$

Fluid gut balance was significantly greater in the rice dextrin ORS group during the first six hours of the rehydration phase. When analyzed across the different periods of study, the mean fluid balance for the rice dextrin ORS group was greater (55.2±3.1 mL/kg) than the glucose ORS group (41.4±3.2 mL/kg).

Although the sodium content of the glucose ORS was higher, there was no difference in net sodium gut balance between the groups during any of the four time periods over 0-48 hours. Surprisingly, mean balance was higher in the rice dextrin ORS group when that parameter was evaluated across the duration of the study.

Potassium gut balance in the rice dextrin ORS group was statistically greater than the glucose ORS group during the first six hours of therapy. Throughout the remaining three time periods of the study there was a trend of greater gut balance in the rice dextrin ORS group compared to the glucose ORS group.

The results of the foregoing rice dextrin ORS and glucose ORS study indicate that both formulations were effective in restoring hydration. However, the balance studies demonstrate that the rice dextrin ORS of the instant invention was more effective than glucose ORS in treating diarrhea inasmuch as infants fed rice dextrin ORS had significantly lower stool output (Table 15) and greater water and potassium balance (Table 16) during the initial six hour rehydration period than glucose ORS with a trend in this direction continuing through the three time periods up to 48 hours. Sodium balance was not different between the two groups (Table 16) indicating that the rice dextrin ORS, although containing lower sodium levels, was nevertheless as efficient in promoting sodium absorption as the glucose ORS which had a higher sodium level (Table 12).

What is claimed is:

1. An improved oral rehydration solution containing electrolytes and carbohydrate wherein the improvement comprises using rice dextrin as the carbohydrate component, said rice dextrin having a glucose polymer profile of from 50 to 90% short chain glucose polymers of 2 to 6 glucose unit, and having a protein or other particulate content of no more than one tenth of one percent.

2. The oral rehydration solution of claim 1 having from 55 to 80% short chain glucose polymers.

3. The oral rehydration solution of claim 1 having from 65 to 75% glucose units.

4. A process for clarifying rice dextrin comprising the steps of
   (a) filtering the solubilized rice carbohydrate fraction obtained from rice flour by enzymatic hydrolysis at neutral pH using filter aid at 35° C. to 50° C.; and then
   (b) subjecting the filtrate to a second filtration using filter aid and activated carbon at temperatures above 80° C.

5. The process of claim 4 wherein the clarified rice dextrin has a glucose polymer profile of from 50 to 90% short chain glucose polymers of 2 to 6 glucose units, and having a protein or other particulate content of no more than one tenth of one percent.

6. The process of claim 4 where the pH of the second filtrate is adjusted to 4.0-4.8 and spray dried to provide rice dextrin having a glucose polymer profile of from 50 to 90% short chain glucose polymers of 2 to 6 glucose units.

7. The process of claim 4 where the pH of the second filtrate is adjusted to 4.5 and spray dried to provide rice dextrin having a glucose polymer profile of from 50 to 90% short chain glucose polymers of 2 to 6 glucose units.

8. A method for treating diarrhea which comprises administering to a patient in need of such treatment an oral rehydration solution containing electrolytes and carbohydrate wherein said carbohydrate is rice dextrin having a glucose polymer profile of from 50 to 90% short chain glucose polymer of 2 to 6 glucose units, and having a protein or other particulate content of no more than one tenth of one percent.

* * * * *